United States Patent
Fisk et al.

(10) Patent No.: US 8,933,260 B2
(45) Date of Patent: Jan. 13, 2015

(54) PROCESS FOR PREPARING ALKOXYCARBONYL ISOTHIOCYANATE

(71) Applicant: Dow AgroSciences LLC, Indianapolis, IN (US)

(72) Inventors: Jason S. Fisk, Freeland, MI (US); Douglas C. Bland, Midland, MI (US); George J. Frycek, Midland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 14/049,820

(22) Filed: Oct. 9, 2013

(65) Prior Publication Data

US 2014/0100381 A1 Apr. 10, 2014

Related U.S. Application Data

(60) Provisional application No. 61/711,868, filed on Oct. 10, 2012.

(51) Int. Cl.
*C07C 331/32* (2006.01)

(52) U.S. Cl.
CPC .................................... *C07C 331/32* (2013.01)
USPC ............................................................ 558/19

(58) Field of Classification Search
USPC .......................................................... 558/19
See application file for complete search history.

(56) References Cited

U.S. PATENT DOCUMENTS

| | | |
|---|---|---|
| 4,659,853 A | 4/1987 | Fu et al. |
| 4,778,921 A | 10/1988 | Lewellyn et al. |
| 5,194,673 A | 3/1993 | Wang et al. |
| 8,143,395 B2 | 3/2012 | Bott et al. |

*Primary Examiner* — Kristin Vajda
(74) *Attorney, Agent, or Firm* — Michael R. Asam

(57) ABSTRACT

Provided herein are processes for the preparation of alkoxycarbonyl isothiocyanates from alkyl chloroformates and thiocyanates in toluene by controlling the amounts of water and catalyst.

14 Claims, No Drawings

PROCESS FOR PREPARING ALKOXYCARBONYL ISOTHIOCYANATE

CROSS REFERENCE TO RELATED APPLICATIONS

This application claims the benefit of U.S. Provisional Patent Application Ser. No. 61/711,868 filed Oct. 10, 2012, the disclosure of which is expressly incorporated herein by reference.

BACKGROUND

Provided herein are processes for the preparation of alkoxycarbonyl isothiocyanate.

U.S. Pat. No. 8,143,395 describes a process for the preparation of 5-substituted-8-alkoxy[1,2,4]triazolo[1,5-c]pyrimidin-2-amines efficiently and in high yield by a manufacturing process that avoids hydrazine and cyanogen halide. The first step of the process requires an alkoxycarbonyl isothiocyanate starting material of the formula

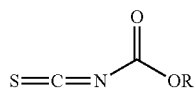

in which R represents $C_1$-$C_4$ alkyl.

U.S. Pat. No. 4,659,853 teaches that alkoxycarbonyl isothiocyanate can be generated using an organic solvent, including aromatic hydrocarbons such as toluene. However, the addition of a co-solvent such as acetonitrile is needed for improvement of reaction rates and yield.

U.S. Pat. No. 4,778,921 teaches that alkoxycarbonyl isothiocyanate can be generated using water alone as the solvent system. U.S. Pat. No. 5,194,673 teaches that co-catalysts such as sodium or potassium acetate accelerate the rate of alkoxycarbonyl isothiocyanate generation when using water alone as the solvent system. However, isolating alkoxycarbonyl isothiocyanate from aqueous solutions generally results in decomposition and thus lower usable yields of product.

It would be advantageous to produce alkoxycarbonyl isothiocyanates efficiently, at faster rate and in high yield free of the decomposition products such as hydrogen sulfide, carbamates and alkyl chlorides.

SUMMARY

Provided herein are processes for the preparation of alkoxycarbonyl isothiocyanates. More particularly, provided herein are improved processes for the preparation of an alkoxycarbonyl isothiocyanate of the formula

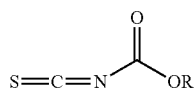

in which R represents $C_1$-$C_4$ alkyl which comprises contacting a salt of thiocyanate ($^-$SCN) with an alkyl chloroformate in toluene solvent in the presence of a) from about 0.01 to about 1.00 molar equivalents of water and b) from about 0.01 to about 1.00 molar equivalents of a catalyst comprising a six-membered mononuclear or ten-membered fused polynuclear aromatic, heterocyclic compound having 1 or 2 nitrogen atoms as the only heteroatoms in the ring, at a temperature from about 0° C. to about 110° C.

DETAILED DESCRIPTION

The term alkyl and derivative terms such as alkoxy, as used herein refer to straight chain or branched chain groups. Exemplary alkyl groups are methyl, ethyl, propyl, 1-methyl-ethyl, butyl, 1,1-dimethylethyl and 1-methylpropyl. In some embodiments, the alkyl group is methyl or ethyl.

Provided herein are processes for the preparation of alkoxycarbonyl isothiocyanates from alkyl chloroformates and thiocyanates. This is accomplished by contacting at least one equivalent and, in certain embodiments, a slight excess of the $C_1$-$C_4$ alkyl chloroformate with the thiocyanate salt in toluene solvent. Any alkali metal or alkaline earth metal thiocyanate may be used. In certain embodiments, the sodium and potassium salts are utilized. In certain embodiments, ammonium thiocyanate is utilized.

Improved yields and reaction rates are dependent on the amount of water and catalyst employed. The catalyst is comprised of a six-membered mononuclear or ten-membered fused polynuclear aromatic, heterocyclic compound having 1 or 2 nitrogen atoms as the only heteroatoms in the ring. Exemplary catalysts include pyridine, quinoline, pyrimidine, pyrazine, quinoxaline and the like, which may be substituted with alkyl, halo and alkoxy groups, provided the derivatives are unsubstituted in the 2-position. From about 0.01 to about 1.00 molar equivalents of a catalyst are employed. In certain embodiments, from about 0.01 to about 0.03 molar equivalents of catalyst are employed. With respect to water, from about 0.01 to about 1.00 molar equivalents are added. In certain embodiments, from about 0.05 to about 0.1 molar equivalents are added.

The reaction is conducted from about 0° C. to about 110° C. In some embodiments, the reaction is conducted from about 20° C. to about 40° C. The product is isolated by conventional techniques.

In an exemplary reaction, sodium thiocyanate is suspended in a solution consisting of toluene, water and pyridine. The mixture is treated with ethyl chloroformate and stirred until the sodium thiocyanate has been consumed. The sodium chloride is removed either by filtration or by aqueous extraction. The product ethoxycarbonyl isothiocyanate can be isolated by vacuum distillation or, after assaying for ethoxycarbonyl isothiocyanate, the reaction mixture can be used as is.

The alkyl chloroformate has the following formula:

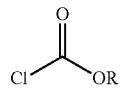

wherein R is as previously defined for the alkoxycarbonyl isothiocyanate.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example 1

Preparation of ethoxycarbonyl isothiocyanate

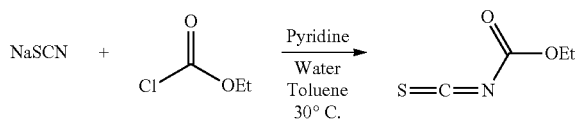

A 1-liter (L) jacketed reactor was charged with sodium thiocyanate (39.1 grams (g), 0.48 moles (mol)) and 310 g of toluene. The solution was heated to 30° C. and treated with pyridine (0.4 g, 0.005 mol) and water (0.9 g, 0.05 mol). Then ethyl chloroformate (52.9 g, 0.49 mol) was added drop-wise to the solution over 40 minutes (min). The solution was left to stir for 3 hours (h), at which time nearly all the ethyl chloroformate had been consumed as determined by gas chromatography (GC). The solution was then filtered and analyzed by GC affording the final product in 99% yield as determined using a quantitative internal standard method.

Comparative Example 2

Preparation of ethoxycarbonyl isothiocyanate with Minimal Water

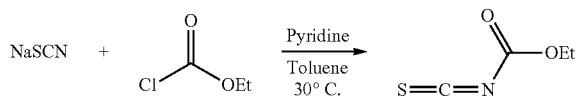

A 1-L jacketed reactor was charged with sodium thiocyanate (39.1 g, 0.48 mol) and 310 g of toluene. The solution was dried via vacuum distillation (70° C., 230 mmHg) until it contained approximately 50 ppm water as determined by Karl Fischer titration. The solution was subsequently cooled to 30° C. and treated with pyridine (0.4 g, 0.005 mol). Then ethyl chloroformate (52.9 g, 0.49 mol) was added drop-wise to the solution over 40 min. The solution was left to stir for 22 h, at which time nearly all the ethyl chloroformate had been consumed as determined by GC. The solution was then filtered and analyzed by GC affording the final product in 63% yield as determined using a quantitative internal standard method.

What is claimed is:

1. A process for the preparation of an alkoxycarbonyl isothiocyanate of the formula

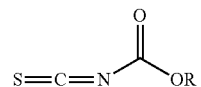

wherein R represents $C_1$-$C_4$ alkyl
which comprises contacting a salt of thiocyanate ($^-$SCN) with an alkyl chloroformate in toluene solvent in the presence of a) from about 0.01 to about 1.00 molar equivalents of water and b) from about 0.01 to about 1.00 molar equivalents of a catalyst comprising a six-membered mononuclear or ten-membered fused polynuclear aromatic, heterocyclic compound having 1 or 2 nitrogen atoms as the only heteroatoms in the ring, at a temperature from about 0° C. to about 110° C., wherein the alkyl chloroformate has the following formula:

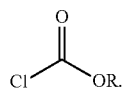

2. The process of claim 1, wherein R is methyl or ethyl.
3. The process of claim 2, wherein R is ethyl.
4. The process of claim 1, wherein the salt of thiocyanate is a sodium, potassium or ammonium salt.
5. The process of claim 4, wherein the salt of thiocyanate is a sodium salt.
6. The process of claim 1, wherein the catalyst is pyridine, quinoline, pyrimidine, pyrazine, or quinoxaline optionally substituted with one or more alkyl, halo, or alkoxy groups, wherein the pyridine, quinoline, pyrimidine, pyrazine, or quinoxaline is unsubstituted at the 2-position.
7. The process of claim 6, wherein the catalyst is pyridine.
8. The process of claim 1, wherein about 0.05 to about 0.1 molar equivalents of water are employed.
9. The process of claim 8, wherein about 0.1 molar equivalents of water are employed.
10. The process of claim 1, wherein about 0.01 to about 0.03 molar equivalents of catalyst are employed.
11. The process of claim 10, wherein about 0.01 equivalents of catalyst are employed.
12. The process of claim 1, wherein the temperature is from about 20° C. to about 40° C.
13. The process of claim 12, wherein the temperature is about 30° C.
14. The process of claim 1, wherein
   a. R is methyl or ethyl;
   b. the salt of thiocyanate is a sodium, potassium or ammonium salt;
   c. the catalyst is pyridine, quinoline, pyrimidine, pyrazine, or quinoxaline optionally substituted with one or more alkyl, halo, or alkoxy groups, wherein the pyridine, quinoline, pyrimidine, pyrazine, or quinoxaline is unsubstituted at the 2-position;
   d. about 0.05 to about 0.1 molar equivalents of water are employed;
   e. about 0.01 to about 0.03 molar equivalents of catalyst are employed; and
   f. wherein the temperature is from about 20° C. to about 40° C.

* * * * *